US010702174B2

(12) United States Patent
Fasciano

(10) Patent No.: US 10,702,174 B2
(45) Date of Patent: Jul. 7, 2020

(54) MEDICAL MONITOR USER INTERFACE

(75) Inventor: Robert W. Fasciano, Middleton, MA (US)

(73) Assignee: Integra Lifesciences Corporation, Plainsboro, NJ (US)

( * ) Notice: Subject to any disclaimer, the term of this patent is extended or adjusted under 35 U.S.C. 154(b) by 1958 days.

(21) Appl. No.: 11/769,168

(22) Filed: Jun. 27, 2007

(65) Prior Publication Data
US 2009/0005703 A1 Jan. 1, 2009

(51) Int. Cl.
A61B 5/03 (2006.01)
A61B 5/00 (2006.01)
G16H 40/63 (2018.01)

(52) U.S. Cl.
CPC .............. A61B 5/031 (2013.01); A61B 5/742 (2013.01); A61B 5/7435 (2013.01); A61B 5/7445 (2013.01); A61B 5/7475 (2013.01); G16H 40/63 (2018.01); A61B 5/0002 (2013.01)

(58) Field of Classification Search
CPC ....... A61B 5/0002; A61B 5/031; A61B 5/742; A61B 5/7435; A61B 5/7445; A61B 5/7475; G06F 19/3406; G16H 40/63
USPC ........................................ 600/484, 486, 561
See application file for complete search history.

(56) References Cited

U.S. PATENT DOCUMENTS 2,396,351 A 3/1946 Thompson
3,886,948 A 6/1975 Hakim
3,960,142 A 6/1976 Elliott et al.
3,976,278 A 8/1976 Dye et al.
4,114,603 A 9/1978 Wilkinson
4,135,509 A 1/1979 Shannon
(Continued)

FOREIGN PATENT DOCUMENTS

AU 729 467 B2 2/2001
DE 42 11 045 A1 10/1993
(Continued)

OTHER PUBLICATIONS

Shapiro, K. et al.: "Characterization of Clinical CSF Dynamics and Neural Axis Compliance Using the Pressure-Volume Index: I. The Normal Presure-Volume Index", Annals of Neurology, vol. 7, No. 6, Jun. 1980; pp. 0364-5134.
(Continued)

Primary Examiner — Daniel L Cerioni
(74) Attorney, Agent, or Firm — Mintz Levin Cohn Ferris Glovsky and Popeo, P.C.

(57) ABSTRACT

Methods and devices useful for monitoring a patient and for monitoring and displaying the value of a physiological parameter are disclosed. In one embodiment, a user interface for a medical monitoring device is provided. The user interface can have a monitoring screen with a current value screen and a trend screen. The current value screen can display a graphical representation of a value of a physiological parameter over time, e.g., over a first time period, and the trend screen can display a graphical representation of a mean value of the parameter over time, e.g., over a second time period. In some embodiments, an out-of-limit condition for the parameter can be indicated with shading. In yet other embodiments, the user interface can provide an event marking screen, which can provide the ability to mark events on a historical trend screen that displays a value of the parameter over time.

13 Claims, 8 Drawing Sheets

(56) References Cited

U.S. PATENT DOCUMENTS

| | | | |
|---|---|---|---|
| 4,332,255 A | 6/1982 | Hakim et al. |
| 4,387,715 A | 6/1983 | Hakim et al. |
| 4,407,296 A | 10/1983 | Anderson |
| 4,421,124 A | 12/1983 | Marshall |
| 4,543,088 A | 9/1985 | Bootman et al. |
| 4,551,128 A | 11/1985 | Hakim et al. |
| 4,552,552 A | 11/1985 | Polaschegg et al. |
| 4,556,086 A | 12/1985 | Raines |
| 4,576,181 A | 3/1986 | Wallace et al. |
| 4,592,339 A | 6/1986 | Kuzmak et al. |
| 4,595,390 A | 6/1986 | Hakim et al. |
| 4,615,691 A | 10/1986 | Hakim et al. |
| 4,651,746 A | 3/1987 | Wall |
| 4,711,249 A | 12/1987 | Brooks |
| 4,727,887 A | 3/1988 | Haber |
| 4,772,257 A | 9/1988 | Hakim et al. |
| 4,781,680 A | 11/1988 | Redmond et al. |
| 4,785,822 A | 11/1988 | Wallace |
| 4,820,265 A | 4/1989 | DeSatnick et al. |
| 4,840,615 A | 6/1989 | Hancock et al. |
| 4,893,630 A * | 1/1990 | Bray, Jr. ................ 600/484 |
| 4,937,037 A * | 6/1990 | Griffiths et al. .......... 345/36 |
| 5,004,472 A | 4/1991 | Wallace |
| 5,009,662 A | 4/1991 | Wallace et al. |
| 5,021,046 A | 6/1991 | Wallace |
| 5,120,313 A | 6/1992 | Elftman |
| 5,121,470 A | 6/1992 | Trautman |
| 5,163,904 A | 11/1992 | Lampropoulos et al. |
| 5,201,753 A | 4/1993 | Lampropoulos et al. |
| 5,226,416 A | 7/1993 | Bethune et al. |
| 5,262,944 A | 11/1993 | Weisner et al. |
| 5,280,789 A | 1/1994 | Potts |
| 5,285,792 A | 2/1994 | Sjoquist et al. |
| 5,396,899 A | 3/1995 | Strittmatter |
| 5,425,713 A | 6/1995 | Taylor et al. |
| 5,431,629 A | 7/1995 | Lampropoulos et al. |
| 5,438,983 A | 8/1995 | Falcone |
| 5,449,345 A | 9/1995 | Taylor et al. |
| 5,464,012 A | 11/1995 | Falcone |
| 5,490,514 A | 2/1996 | Rosenberg |
| 5,522,387 A | 6/1996 | Simons |
| 5,549,654 A | 8/1996 | Powell |
| 5,591,171 A | 1/1997 | Brown |
| 5,622,869 A | 4/1997 | Lewis et al. |
| 5,701,906 A | 12/1997 | Alcidi et al. |
| 5,711,302 A | 1/1998 | Lampropoulos et al. |
| 5,716,342 A | 2/1998 | Dumbraveanu et al. |
| 5,721,382 A | 2/1998 | Kriesel et al. |
| 5,722,999 A | 3/1998 | Snell |
| 5,724,985 A | 3/1998 | Snell et al. |
| 5,772,599 A | 6/1998 | Nevo et al. |
| 5,785,043 A | 7/1998 | Cyrus et al. |
| 5,797,403 A | 8/1998 | DiLorenzo |
| 5,803,917 A | 9/1998 | Butterfield et al. |
| 5,891,046 A | 4/1999 | Cyrus et al. |
| 5,920,263 A | 7/1999 | Huttenhoff et al. |
| 5,928,182 A | 7/1999 | Kraus et al. |
| 5,935,083 A | 8/1999 | Williams |
| 5,938,669 A | 8/1999 | Klaiber et al. |
| 5,951,485 A | 9/1999 | Cyrus et al. |
| 5,970,801 A | 10/1999 | Ciobanu et al. |
| 5,991,664 A | 11/1999 | Seligman |
| 5,993,395 A | 11/1999 | Shulze |
| 5,993,398 A | 11/1999 | Alperin |
| 6,010,482 A | 1/2000 | Kriesel et al. |
| 6,067,991 A | 5/2000 | Forsell et al. |
| 6,071,267 A | 6/2000 | Zamierowski |
| 6,158,965 A | 12/2000 | Butterfield et al. |
| 6,171,252 B1 | 1/2001 | Roberts |
| 6,238,349 B1 | 5/2001 | Hickey |
| 6,241,661 B1 | 6/2001 | Schluess et al. |
| 6,262,728 B1 | 7/2001 | Alexander |
| 6,305,373 B1 | 10/2001 | Wallace et al. |
| 6,315,769 B1 | 11/2001 | Peer et al. |
| 6,322,502 B1 | 11/2001 | Schoenberg et al. |
| 6,416,291 B1 | 7/2002 | Butterfield et al. |
| 6,424,860 B1 | 7/2002 | Karlsson et al. |
| 6,432,040 B1 | 8/2002 | Meah |
| 6,470,213 B1 | 10/2002 | Alley |
| 6,481,292 B1 | 11/2002 | Reich |
| 6,485,462 B1 | 11/2002 | Kriesel |
| 6,503,208 B1 | 1/2003 | Skovlund et al. |
| 6,589,189 B2 | 7/2003 | Meyerson et al. |
| 6,779,851 B2 | 8/2004 | Bouchiere |
| 7,031,857 B2 * | 4/2006 | Tarassenko et al. ............ 702/67 |
| 7,143,462 B2 | 12/2006 | Hohlbein |
| 7,616,991 B2 | 11/2009 | Mann et al. |
| 8,027,846 B2 | 9/2011 | Schoenberg et al. |
| 2001/0011543 A1 | 8/2001 | Forsell |
| 2002/0016719 A1 | 2/2002 | Nemeth et al. |
| 2002/0138512 A1 | 9/2002 | Buresh et al. |
| 2002/0161291 A1 | 10/2002 | Kianl et al. |
| 2003/0023134 A1 | 1/2003 | Tracey |
| 2003/0093117 A1 | 5/2003 | Saadat |
| 2003/0114836 A1 | 6/2003 | Estes et al. |
| 2003/0144711 A1 | 7/2003 | Pless et al. |
| 2003/0172940 A1 | 9/2003 | Rogers et al. |
| 2003/0225371 A1 | 12/2003 | Hadzic et al. |
| 2004/0039256 A1 * | 2/2004 | Kawatahara et al. ........ 600/300 |
| 2004/0054295 A1 | 3/2004 | Ramseth |
| 2004/0082904 A1 | 4/2004 | Houde et al. |
| 2004/0087863 A1 | 5/2004 | Eide |
| 2004/0143212 A1 | 7/2004 | Trombley et al. |
| 2004/0193045 A1 | 9/2004 | Scarborough et al. |
| 2004/0215159 A1 | 10/2004 | Forsell |
| 2004/0215492 A1 | 10/2004 | Choi |
| 2004/0225203 A1 | 11/2004 | Jemison et al. |
| 2004/0249421 A1 | 12/2004 | Harel et al. |
| 2004/0260319 A1 | 12/2004 | Egle |
| 2004/0267377 A1 | 12/2004 | Egle |
| 2005/0065450 A1 | 3/2005 | Stuebe et al. |
| 2005/0070778 A1 | 3/2005 | Lackey et al. |
| 2005/0137488 A1 * | 6/2005 | Henry ................. A61N 1/3702 600/513 |
| 2005/0143668 A1 | 6/2005 | Lu et al. |
| 2005/0203360 A1 * | 9/2005 | Brauker et al. ............. 600/345 |
| 2005/0240144 A1 | 10/2005 | Wassemann et al. |
| 2006/0064136 A1 | 3/2006 | Wang |
| 2006/0149161 A1 | 7/2006 | Wilson et al. |
| 2006/0189888 A1 | 8/2006 | Hassler et al. |
| 2006/0199997 A1 | 9/2006 | Hassler et al. |
| 2006/0200009 A1 | 9/2006 | Wekell et al. |
| 2006/0247722 A1 | 11/2006 | Maschino et al. |
| 2007/0156013 A1 | 7/2007 | Birk |
| 2007/0161958 A1 | 7/2007 | Glenn |
| 2008/0096808 A1 | 4/2008 | Scaria |
| 2008/0172072 A1 | 7/2008 | Pool et al. |
| 2008/0221495 A1 | 9/2008 | Steffens et al. |
| 2008/0250341 A1 | 10/2008 | Dlugos et al. |

FOREIGN PATENT DOCUMENTS

| | | |
|---|---|---|
| DE | 9416395 U1 | 12/1994 |
| EP | 0654232 A1 | 5/1995 |
| EP | 0 858 814 A1 | 8/1998 |
| EP | 0876808 A1 | 11/1998 |
| EP | 0941712 A1 | 9/1999 |
| EP | 1600120 A1 | 11/2005 |
| EP | 1649884 A1 | 4/2006 |
| EP | 1676527 A1 | 7/2006 |
| EP | 1 704 833 A2 | 9/2006 |
| EP | 1736123 | 12/2006 |
| EP | 1815881 A1 | 8/2007 |
| EP | 1832252 A2 | 9/2007 |
| EP | 1832253 A1 | 9/2007 |
| EP | 1967168 A2 | 9/2008 |
| FR | 2730158 A1 | 8/1996 |
| GB | 1486822 A | 9/1977 |
| JP | 2004-513681 A | 5/2004 |
| JP | 2004-248793 A | 9/2004 |
| JP | 2004-261583 A | 9/2004 |
| JP | 2004-528123 A | 9/2004 |
| JP | 2004-344649 A | 12/2004 |
| JP | 2006175191 A | 7/2006 |

(56) References Cited

FOREIGN PATENT DOCUMENTS

| | | |
|---|---|---|
| RU | 2117459 C1 | 8/1998 |
| RU | 2002122333 | 4/2004 |
| WO | 97/01370 A1 | 1/1997 |
| WO | 0009047 A1 | 2/2000 |
| WO | 0108597 A1 | 2/2001 |
| WO | 0112078 | 2/2001 |
| WO | 03043534 A2 | 5/2003 |
| WO | 03/059422 A1 | 7/2003 |
| WO | WO-03091841 A2 | 11/2003 |
| WO | 03105732 A1 | 12/2003 |
| WO | 2004/014245 A1 | 2/2004 |
| WO | 2006/018927 A1 | 2/2006 |
| WO | 20061108203 A2 | 10/2006 |
| WO | 2006118793 A2 | 11/2006 |
| WO | 2007070906 A2 | 6/2007 |
| WO | 2008088949 A1 | 7/2008 |
| WO | 2010/083498 A1 | 7/2010 |

OTHER PUBLICATIONS

J.Ekstedt: "CSFS hydrodynamic studies in man, 1. Method of constant pressure CSF infusion", Journal of Neurology, Neurosurgery and Psychiatry; vol. 40, 1977, pp. 105-119.

"User's Manual HD2114.0-HD2134.0, HD2164.0-HD2114B.0, HD2114, 2-HD2134.2, HD2164.2-HD2114B; Rev. 1.0", Oct. 1, 2004, Delta Ohm, Via G. Marconi, 5-35020 Caselle Di Selvazzano(PD)—Italy, XP002376759, pp. 2-6.

Codman Brochure "ICP Express" © *CODMAN & Shurtleff, Inc.*, 2001.

Japanese Office Action dated Jan. 29, 2013 for Application No. 2008-166883 (4 Pages).

Australian Office Action dated Nov. 20, 2012 for Application No. 2008202685 (4 Pages).

Australian Office Action for Application No. 2006202142, dated Mar. 4, 2011. (3 pages).

EPO Search Report dated Jul. 12, 2007, for EP Application No. 07250931.8.

EPO Search Report dated Jul. 23, 2007, for EP Application No. 07250932.6.

European Examination Report dated Dec. 9, 2008 for Application No. EP 06250968.

European Examination Report dated Jul. 23, 2007 for Application No. 06253286.

European Search Report dated Aug. 13, 2009 for Application No. 08251093.

European Search Report dated Dec. 9, 2008 for Application No. 06250968.

European Search Report dated Feb. 10, 2009 for Application No. 07250915.

European Search Report dated Jul. 10, 2009 for Application No. 09250590.8.

European Search Report dated Jun. 19, 2009 for Application No. 09250581.

European Search Report dated Mar. 5, 2006 for Application No. 06250156.4.

European Search Report dated May 2, 2008 for Application No. Ep 06250968.

European Search Report dated Oct. 30, 2006 for Application No. 06253276.

European Search Report dated Sep. 25, 2009 for Application No. 09250590.

European Search Report dated Sep. 25, 2009 for Application No. 09250600.5.

European Search Report for Application No. 10179035.0 dated Dec. 8, 2010. (5 pages).

European Search Report, Application No. 08253986.7, dated Mar. 30, 2009, 5 pages.

European Search Report, Application No. 09250497.6, dated May 13, 2009, 10 pages.

Examination Report dated Feb. 20, 2007 for Application No. 06250156.

Extended EPO Search Report dated Apr. 22, 2009 for Application No. 08250782.

International Search Report and Written Opinion dated Sep. 22, 2008 for Application No. PCT/US2008/053394.

Japanese Office Action for Application No. 2006-174174, dated Oct. 18, 2011. (3 pages).

Partial EPO Search Report dated Jan. 13, 2009 for Application No. 08250782.

Russian Decision to Grant for application No. 2006122627/14(024568) dated Feb. 2, 2012. (6 pages).

Russian Official Action for application No. 2006122627/14(024568) dated Mar. 3, 2010. (4 pages).

Russian Official Action for application No. 2009107266/14(009705) dated Dec. 5, 2012. (4 pages).

"Suga et al., ""Instantaneous Pressure-Volume Relationships and Their Ratio in the Excised, Supported Canine Left Ventricle,"" Circ. Res. 1974, 35, 117-126."

Greenway et al., "Comparison of the Effects of the Heptatic Nerve Stimulation on Arterial Flow, Distriubtion of Arterial Portal Flows and Blood Content in the Livers of Anaesthetized Cats and Dogs," J. Physiol. 1972, 227, 487-501.

Examination Report for EP Application No. 08252220.2, dated Jun. 9, 2016.

\* cited by examiner

FIG. 1 *PRIOR ART*

MEDICAL MONITOR USER INTERFACE

FIELD

The present invention generally relates to methods and devices for monitoring a patient and for monitoring and displaying the value of a physiological parameter.

BACKGROUND

Patient monitoring can take a variety of forms and can gather a wide variety of physiological data. The display of such data, including what is displayed and how it is displayed, can affect the ability of caregivers such as doctors and nurses to interpret and act on it. For example, intracranial pressure is a standard monitoring modality for traumatic brain injury patients. Medical guidelines may prescribe threshold values for intracranial pressure. The guidelines of the Brain Trauma Foundation, for example, indicate that clinical action should be taken to reduce intracranial pressure if it exceeds 20-25 mmHg. However, numerous factors can cause transient changes to intracranial pressure, including patient physiology, monitoring system noise, and actions taken by a caregiver.

To monitor a patient, caregivers use monitoring devices such as the Codman ICP Express, which is shown in FIG. 1. As shown, it has a display of intracranial pressure and a display of systolic and diastolic values for the intracranial pressure, as well as an alarm. A caregiver can look at the display to ascertain the intracranial pressure. Caregivers also use charts, e.g., a caregiver can manually record an event in a chart associated with a patient.

Improved methods and devices for display of intracranial pressure would allow for a more complete picture of a patient's condition, e.g., to assist in clinical decision making. Moreover, such considerations are applicable not just to intracranial pressure, but to a wide variety of patient monitoring modalities involving other physiological parameters. Accordingly, there is a need for improved devices and methods for monitoring a patient and for monitoring and displaying the value of a physiological parameter.

SUMMARY

In one embodiment, a user interface for a medical monitoring device is provided. The user interface can include a current value screen for displaying a graphical representation of a value of a physiological parameter (e.g., intracranial pressure or other parameter measured from a patient) over a first time period. The user interface can also include a trend screen for displaying a graphical representation of a mean value of the physiological parameter over a second time period. The current value screen and the trend screen can each be displayed on a monitoring screen. The graphical representation drawn displayed on the current value screen can be a graph line, and the graphical representation displayed on the trend screen can be a trendline, which can be similar to or different from the graph line in appearance. In some embodiments, the current value screen can be adapted to indicate an out-of-limit condition for those times when the value of the physiological parameter exceeds a predetermined threshold by shading a region outside of the predetermined limits (for example, a region between a graph line and a threshold line), and/or the trend screen can be adapted to indicate an out-of-limit condition for those times when the mean value of the physiological parameter exceeds a predetermined threshold by shading a region outside of the predetermined limits (for example, a region between a trendline and a threshold line).

In some embodiments, the user interface can include an input device. The input device, for example, can receive user input to select a length of the aforementioned second time period. The user interface can also include processing circuitry for comparing a value of the physiological parameter to a threshold value to detect an out-of-limit condition, and for sending signals to the monitoring screen to display the trend screen only when the processing circuitry detects the out-of-limit condition. Further, the user interface can include an event marker disposed on the graphical representation that is displayed on the trend screen. The event marker can be disposed at a point corresponding to a time at which a medically-related event occurred, the time falling within the aforementioned second time period.

Another exemplary user interface for medical monitoring device can include a trend screen for displaying a graphical representation of a value of a physiological parameter (e.g., intracranial pressure or other parameter measured from a patient) over a time period. The user interface can also include an event marker disposed on the graphical representation at a point corresponding to a time at which a medically-related event occurred, the time falling within the time period. The event marker can be, for example, an event line or an event icon, and can be associated with a start or an end of an out-of-limit or alarm condition. In some embodiments, the user interface can include processing circuitry that can calculate a mean value of the physiological parameter, and the graphical representation displayed on the trend screen can be a graphical representation of the mean value of the physiological parameter over the time period. The user interface can also include a monitoring screen configured to display the trend screen and a current value screen.

A number of further variations and additional features are possible. For example, the user interface can include processing circuitry to calculate a mean value of the physiological parameter, and the trend screen can be adapted to display a graphical representation of the mean value of the physiological parameter for the time period. The user interface can include a pointing device that is configured to allow the user to select an event marker. A marked event information screen can be provided for displaying information about the selected event marker.

In other aspects, methods for monitoring a physiological parameter are provided. In one embodiment, an exemplary method includes receiving data representing the value of a physiological parameter (e.g., intracranial pressure or other parameter measured from a patient) over time. The method can further include displaying, on a monitoring screen, a current value screen and a trend screen and drawing, on the current value screen, a graphical representation (e.g., a graph line) of a value of the physiological parameter over a first time period. The method can further include determining a mean value of the physiological parameter over time, and drawing, on the trend screen, a graphical representation (e.g., a trendline) of the mean value of the physiological parameter over a second time period.

The method can also provide an indication of an out-of-limit condition. For example, the method can include comparing a value of the physiological parameter to a threshold value to detect an out-of-limit condition. The out-of-limit condition can occur when the current value exceeds the threshold value. In some embodiments, the trend screen can be displayed only when the out-of-limit condition is detected. In other embodiments, the method can include shading a region on the trend screen between the trendline and a threshold line (which can correspond to a predetermined threshold) to indicate that the mean value of the physiological parameter is an out-of-limit condition. The method can also include shading a region on the current value screen between the graph line and a threshold line (which can correspond to a predetermined threshold) to indicate that the value of the physiological parameter is an out-of-limit condition.

A wide variety of further variations are possible. The method can include redrawing the trend screen in response to user input to change the length of the second time period, and/or marking (e.g., on the trend screen) the graphical representation of the mean value of the physiological parameter with an event marker. The event marker can be disposed at a point corresponding to a time at which a medically-related event occurred, the time falling within the second time period.

Another exemplary method for monitoring a physiological parameter can include receiving data representing the value of a physiological parameter (e.g., intracranial pressure or other parameter measured from a patient) over time. The method can further include drawing, on a trend screen, a graphical representation (e.g., a trendline) of the value of the physiological parameter over a time period, and marking the graphical representation with an event marker. The event marker can be disposed at a point corresponding to a time (e.g., within the time period) at which a medically-related event occurred. In some embodiments, the event marker can include an event icon that is associated with a point on the graphical representation or trendline. For example, the event marker can be associated with a start or an end of an out-of-limit condition. In other embodiments, the method can include receiving input from a user to select a type of event for marking, and marking the graphical representation with an event marker. The event marker can be associated with the type of event selected by the user. The method can further include receiving input from a user to select the event marker and displaying information about the event associated with the selected event marker. The information can include, for example, the time at which the medically-related event occurred.

A wide variety of further variations are possible. For example, the method can also include drawing, on a current value screen, a graphical representation of a value of the physiological parameter over a second time period. Further, a mean value of the physiological parameter over time can be determined, and a graphical representation (e.g., a trendline) of the mean value of the physiological parameter over the time period can be drawn on the trend screen. The aforementioned current value screen and the trend screen can each be drawn on part of a monitoring screen.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure.

The present application discloses methods and devices useful for monitoring a patient and for displaying and monitoring a physiological parameter. While in many cases the description uses intracranial pressure as an exemplary physiological parameter, this is by way of illustration only. The methods and devices described herein can be applied to virtually any monitoring modality and/or physiological parameter.

Figure 1:
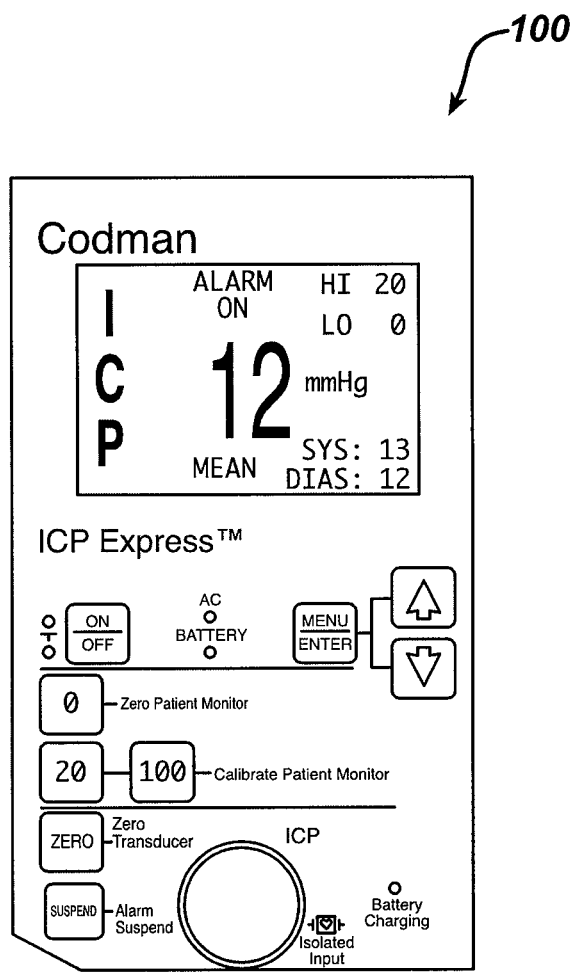
FIG. 1 is a view of a prior art monitor.
Figure 2:
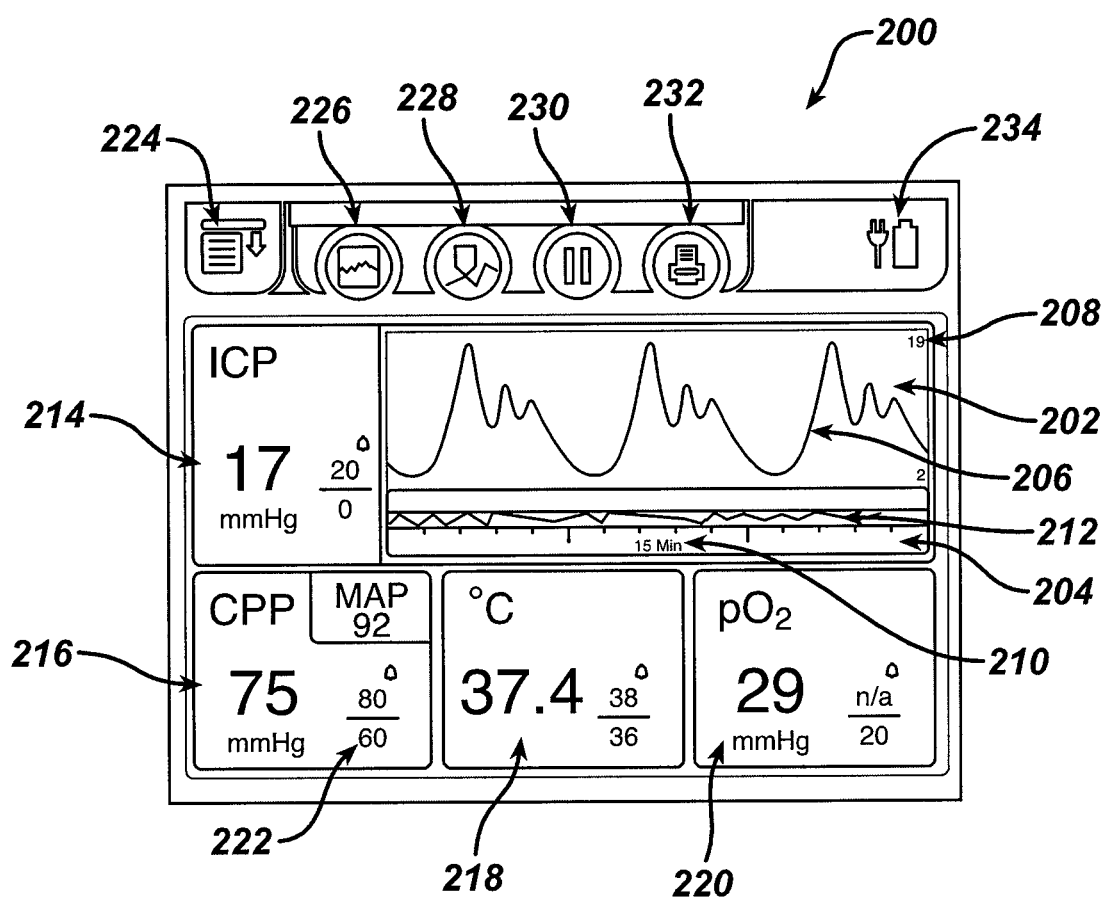
FIG. 2 is a view of an exemplary user interface for a medical monitoring device having a monitoring screen that displays a graphical representation of a current value screen and a trend screen.

FIG. 2 shows one exemplary embodiment of a user interface for a medical device which has a monitoring screen 200 displaying a current value screen 202 and a trend screen 204. In this example, the current value screen 202 and the trend screen 204 display intracranial pressure, e.g., in units of mmHg, but as previously mentioned, any other physiological parameter can be displayed in appropriate units. The current value screen 202 can display the value of the physiological parameter over a current time period, e.g., about the prior five to ten seconds, or the last few heartbeats of the patient. The current time period can also be a single heartbeat. The displayed values can be based on data received by the monitoring device by any method known in the art, e.g., via a Codman Microsensor ICP Transducer or Integra Camino ICP Transducer. As shown, the value of a physiological parameter (e.g., intracranial pressure) is represented graphically by a graph line 206, however virtually any graphical representation can be used, such as a bar graph or a plot of discrete data points, or other pictorial display. The length of the current time period can be adjustable. In some embodiments, to receive user input of this nature the medical monitoring device can include or couple to an input device, such as a touchscreen, keypad, touchpad, pointing device, mouse, button, knob, dial, and so on. For example, the medical monitoring device can include a touchscreen to allow the time period to be adjusted when a user presses the trend screen or when a user activates a menu or soft button displayed on the monitoring screen. Adjustment of the timescale can allow for various clinical protocols, as such protocols can require tracking of a parameter over different time periods. The vertical scale of the current value screen can also be adjustable in a like manner.

The trend screen 204, which is shown below the current value screen 202 in FIG. 2, can display the value of a physiological parameter over another time period 210. Typically, the time period 210 can be longer than the current time period, e.g., 15 minutes in this example, although virtually any time period can be used. In other embodiments, the time period 210 can be hours, days, or longer, and can be adjustable as described above with respect to the current value screen 202. In many embodiments, the time period 210 can be adapted to the requirements of the particular monitoring protocol of interest. For example, the time period can correspond to a time period pertinent to intracranial pressure monitoring and thereby allow a caregiver to review this time period. As shown in FIG. 2, the trend screen 204 displays a trendline 212 for the physiological parameter, e.g., the mean value of the physiological parameter calculated over a sample period such as every 2-3 seconds, (although the mean value can be calculated over any sample period). Moreover, the trend screen can display a trendline 212 or other graphical representation of the mean value, e.g., bar graph, plotted points, and/or other display features as were previously described with respect the current value screen 202 and the graph line 206. Alternatively, the trend screen 204 can display (e.g., via a trendline) the values of another statistic based on the physiological parameter, e.g., median value, normalized value, systolic value, diastolic value, wave amplitude, and so on.

The monitoring screen 200 can have a wide variety of other features and display a wide variety of other data. For example, as shown in FIG. 2, the monitoring screen 200 can have a textual display 214 for indicating the current average value of the physiological parameter, e.g., the current average intracranial pressure. The monitoring screen 200 can also display values for other physiological parameters so as to allow a more complete picture of a patient's condition. As shown, the monitoring screen includes a textual display 216 for cerebral perfusion pressure CPP (e.g., mean arterial pressure MAP minus intracranial pressure ICP in FIG. 2), a textual display 218 for temperature (e.g., displayed in degrees Celsius in FIG. 2), and a textual display 220 for oxygen saturation $pO_2$ (which can be obtained, for example, with an invasive oxygen sensor or a pulse oximeter coupled to the medical monitoring device). The monitoring screen 200 can display virtually any other physiological parameter susceptible to monitoring, and/or other monitoring screens can be included to accommodate such displays. Out-of-limit or alarm thresholds can be displayed near the textual displays 214-220 (for example, FIG. 2 shows a set of alarm thresholds 222 in which the lower out-of-limit threshold for CPP is 60 and the upper threshold is 80). In some embodiments, such parameters can be accompanied by their own current value screen and/or trend screen. The monitoring screen 200 can also include one or more controls along its top. For example, a menu button 224 can provide access to a menu for changing system configuration and/or activating other features of the medical monitoring device, as well as changing preferences such as timescale settings for the current value screen 202 or trend screen 204. A trend button 226 can activate a historical trend screen which can show the value of a parameter over time, as will be described in more detail below. An event marking button 228 can provide access to an event marking screen for inputting marked events on such a historical trend screen (or the trend screen 204 on the monitoring screen 200). A pause button 230 can provide the ability to temporarily pause or freeze the display, which can be advantageous for training purposes or to examine a particular aspect of the display in more detail. A print button 232 can provide the ability to print the monitoring screen 200 or portions thereof, e.g., an attached printer or a printer integrated into the medical monitoring device. The monitoring screen 200 can also display status indicators. For example, in FIG. 2, a power indicator 234 displays the current charge of a battery in the monitoring device and whether the device is connected to external electrical power.

The relative size and location of the screens depicted in FIG. 2 are exemplary in nature, and one skilled in the art will understand that any of the screens can have virtually any size and virtually any location. In some embodiments, it can be advantageous to size the trend screen 204 such that it is larger than the current value screen 202, or to display the trend screen 204 alone (such as in a mode for reviewing patient history or trends). The user interface can also display the current value screen 202 alone (such as in a mode for monitoring the current value only).

Figure 3:
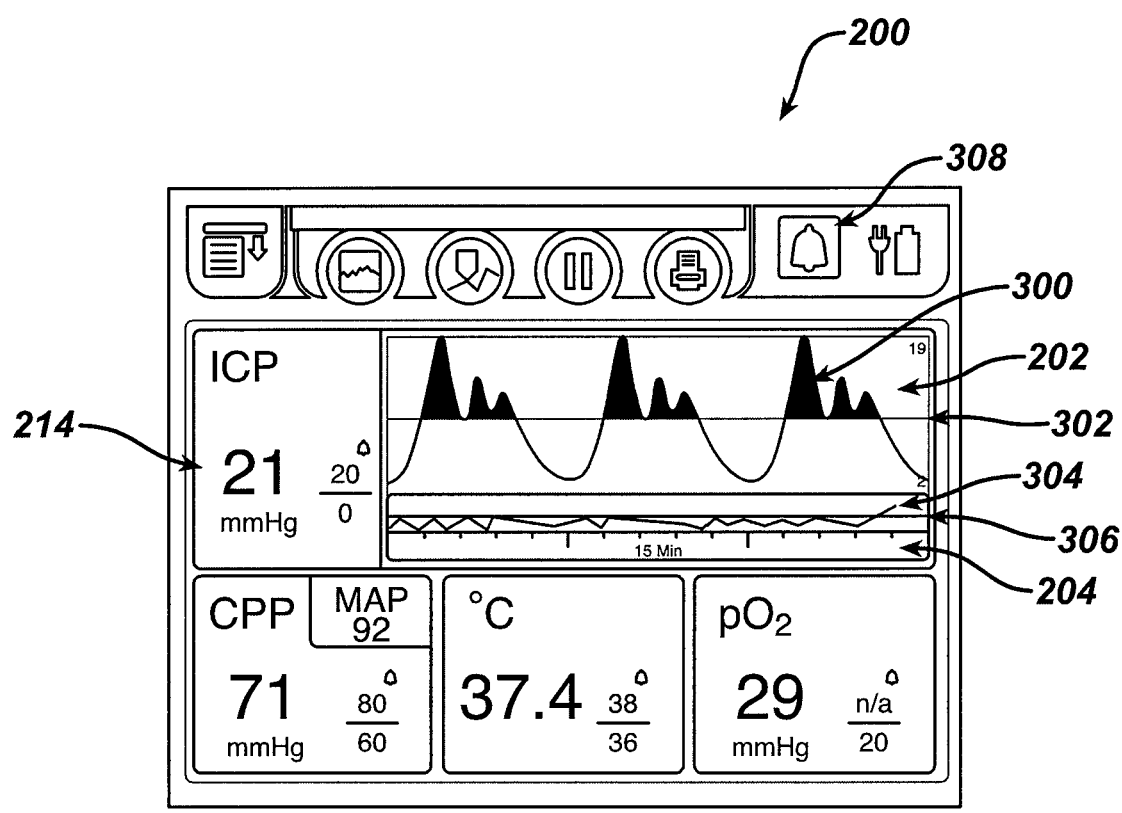
FIG. 3 is a view of the user interface shown in FIG. 2 in which the current value screen and the trend screen display graphical representation of a physiological parameter in an out-of-limit condition.
Figure 4:
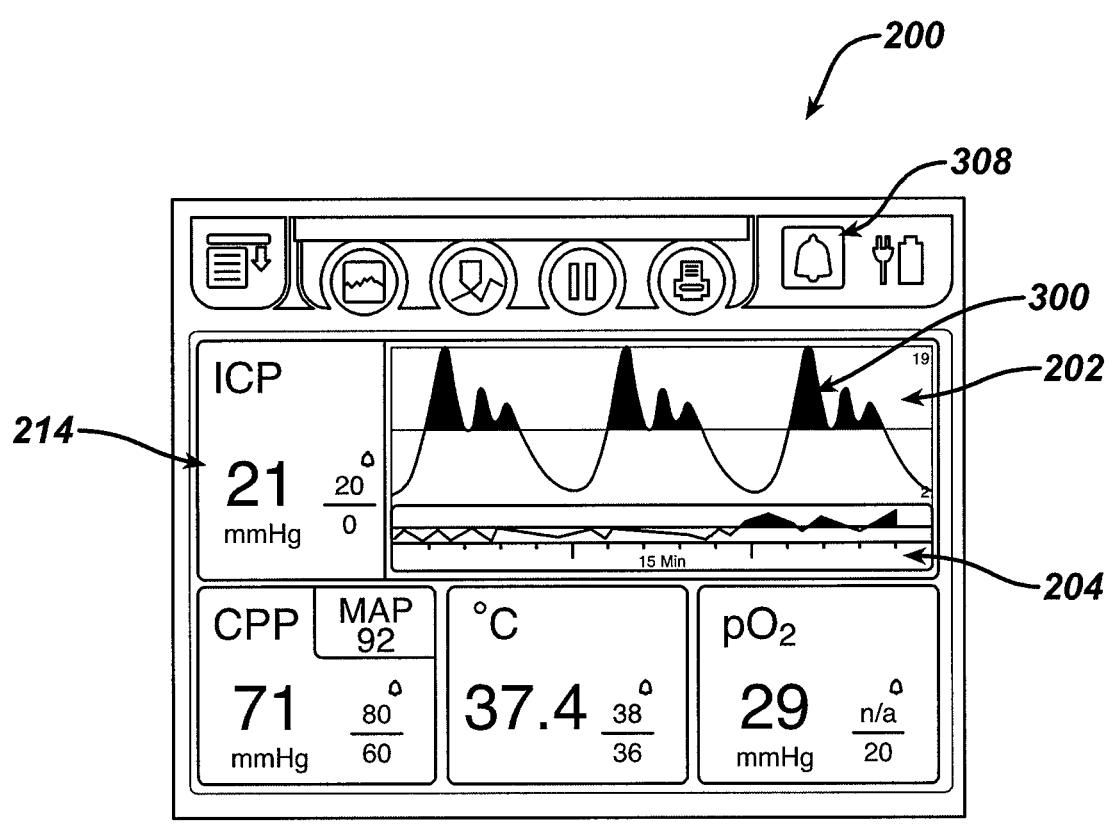
FIG. 4 is a view of the user interface shown in FIG. 2 in which the current value screen and the trend screen display graphical representations of a physiological parameter in an out-of-limit condition that continues over a time period.

FIG. 3 shows the user interface when the medical monitoring device detects an out-of-limit or alarm condition, for example, when a monitored physiological parameter exceeds a threshold value stored in the medical monitoring device. An out-of-limit condition can be displayed in a wide variety of ways, but FIG. 3 shows several different visual alarm indicators. For example, the current value screen 202 can display shading 300 between the graph line 206 and a threshold line 302 to indicate that physiological parameter is above the threshold. The shading 300 can also highlight the magnitude by which the value of the physiological parameter exceeds the threshold line 302, e.g., the shading on the current value screen 202 can provide a visual indication of how the last few heartbeats compare to the a threshold 302. The shading 300 can be any color, and can be solid, patterned, flashing, and so on. The trend screen 204 can also display shading 304 between the trendline 212 and a threshold line 306, which can be a set by a user or be a predetermined level. With respect to the trend screen 204, the shading can indicate the length of time during which the physiological parameter has been above the threshold 306, as well as highlight the magnitude by which the value of the physiological parameter has exceeded the threshold 306 during that time. For example, FIG. 3 shows the user interface about 30 seconds after the onset of an out-of-limit condition. FIG. 4 shows the user interface of FIG. 3 after the out-of-limit condition has persisted for about five minutes. The shading (e.g., the shading 304 on the trend screen 204, and/or the shading 300 on the current value screen 202) can allow a caregiver to determine the time at which the out-of-limit condition began and/or to assess the patient's recent history, which can be advantageous when a caregiver was not available at the onset of the out-of-limit condition. The shading can also allow a caregiver to identify transient out-of-limit conditions and assess their significance. In some embodiments, the trend screen 204 can appear only when the physiological parameter is in an out-of-limit condition (e.g., the current value screen can be shown alone at other times), while in other embodiments the trend screen 204 can be always present on the monitoring screen 200. The user interface can provide another visual indicator of an out-of-limit condition by flashing the textual display 214 that shows the current average of the physiological parameter. In addition, an alarm silence button 308 can be provided, e.g., for silencing an audible alarm in those embodiments in which the monitoring device includes an audible alarm for indicating an out-of-limit condition. In many embodiments, the alarm silence button can appear only when the monitoring device detects an out-of-limit condition.

Figure 5:
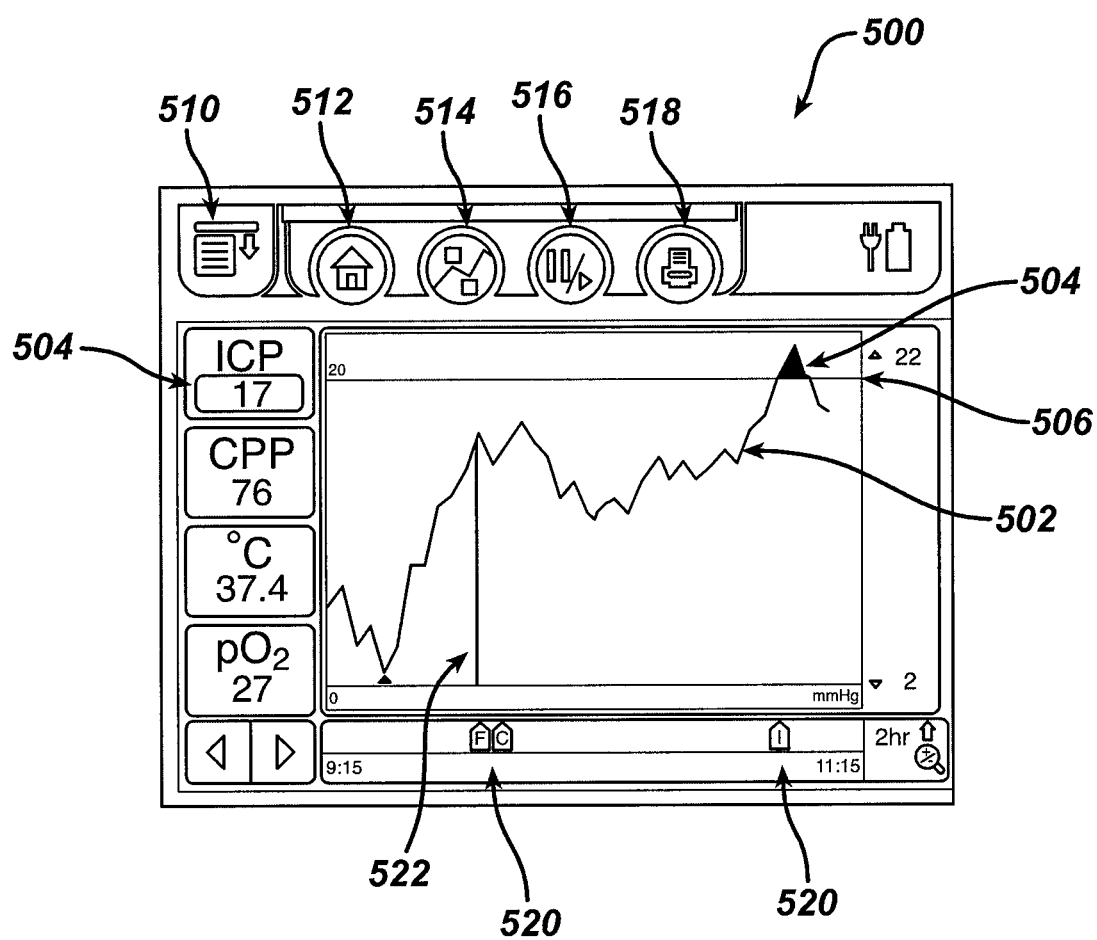
FIG. 5 is a view of a historical trend screen for the user interface shown in FIG. 2 which displays a graphical representation a value of a physiological parameter over time and event markers disposed on the graphical representation.

As previously mentioned, the user interface can include a separate trend screen (e.g., separate from the monitoring screen 200) such as a historical trend screen. The historical trend screen can be accessible via the historical trend screen button 226 on the monitoring screen 200, as previously mentioned. As shown in FIG. 5, in one embodiment a historical trend screen 500 displays a trendline 502 (although any other graphical representation is possible) indicating the value of a physiological parameter over a period of time and allows a caregiver to review a patient's history with respect to a monitored physiological parameter. In this example, the historical trend screen 500 displays the mean value of intracranial pressure over a two-hour time period. It should be noted that while for clarity the trend screen 204 shown in FIG. 2 and the historical trend screen 500 shown in FIG. 5 are differentiated herein by the term "historical," in some embodiments the trend screen 204 and the historical trend screen 500 can cover similar or the same time period, and in some embodiments the trend screen 204 can cover a longer period of time than the historical trend screen 500. Moreover, the historical trend screen 500 can have any of the features previously described with respect to the trend screen 204. For example, the time period shown on the historical trend 500 screen can be adjusted, and/or the historical trend screen 500 can display shading 504 between the trendline 502 and a threshold line 506 to indicate an out-of-limit condition. The historical trend screen 500 can also include a textual display 508 of the mean value of the physiological parameter, as well as a menu button 510, home button 512 that returns the user to monitoring screen 200, a peak button 514 that will turn on or off numerical representations of local extreme values, a pause button 516, and a print button 518.

The historical trend screen 500 can display event markers 520 which indicate the time at which an event occurred. Typically such events are medically-related events, such as the administration of a drug by a caregiver, the adjustment of a sensor that monitors intracranial pressure, the taking of the patient's temperature, caregiver observations, and so on. In this way, the user interface can allow for correlation between a monitored parameter and external events. The event markers 520 can have virtually any form, but as shown in FIG. 5 the event markers 520 are icons disposed at the bottom of the historical trend screen 500. A marked event line 522 can connect the icon to the trendline 502. While in some embodiments all event markers 520 can be identical, in other embodiments the event markers 520 can include one or more of a variety of symbols representing an event category, can be color-coded, and/or can otherwise be distinct for different types of events. Although event marking has been described thus far with respect to the historical trend screen 500, in some embodiments the trend screen 204 displayed on the monitoring screen 200 can display event markers, e.g., in addition to or instead of event marking on the historical trend screen 500.

Figure 6:
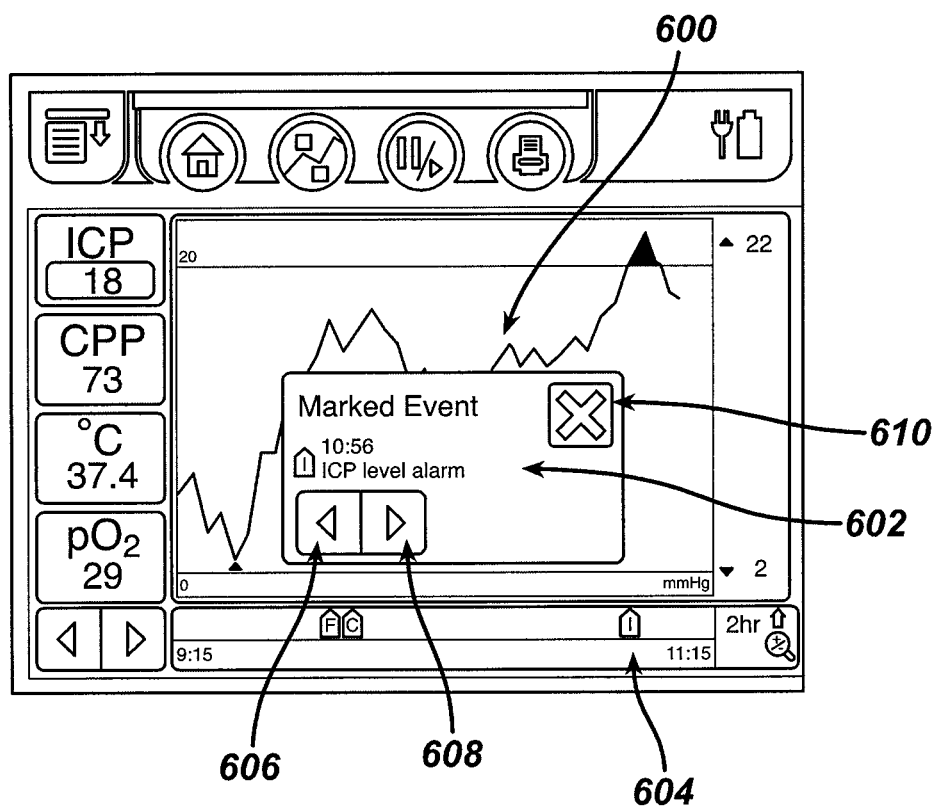
FIG. 6 is a view of an event marking information screen for the user interface shown in FIG. 1 which displays information about a selected marked event.

The user interface can display a marked event information screen upon selection of a event marker, e.g., via a touchscreen or pointing device. FIG. 6 shows one example of a marked event information screen 600. The marked event information screen 600 can display information 602 about a selected marked event 604, and can be displayed as a window overlying the historical trend screen 500 or the monitoring screen 200. The information 602 can include the type of marked event, the time at which the event occurred, and/or other information which may have been entered by a caregiver. In some cases, the information 602 can include the value of the monitored physiological parameter at that point in time. A previous event button 606 and next event button 608 can allow a user to scroll through the marked events 520 on the historical trend screen 500. The marked event information screen 600 can also have a control button 610 for closing the marked event information screen 600.

Figure 7:
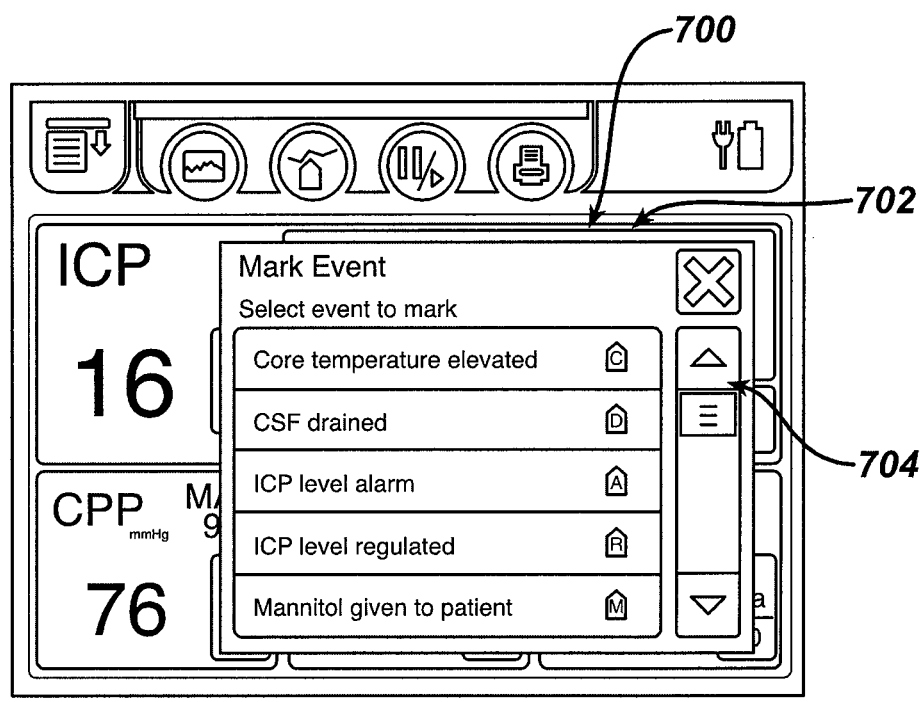
FIG. 7 is a view of an event marking screen for the user interface shown in FIG. 2 for receiving user input to mark events.

Marking of events can occur in a variety of ways. For example, at the onset or end of an out-of-limit condition, the user interface can automatically mark a trendline with an event marker. In other embodiments, the user interface can include an event marking screen to allow a user to enter a marked event manually. FIG. 7 depicts an exemplary event marking screen 700 for manually entering marked events. The event marking screen 700 can be displayed, for example, upon user selection of the event marking button 228 on the monitoring screen 200, as previously mentioned in connection with FIG. 2. As shown in FIG. 7, the event marking screen 700 can be displayed as an window overlying the historical trend screen 500 or the monitoring screen 200. The event marking screen 700 can include one or more events in a list 702 accessed by a scroll control 704. The events in the list 702 can be predetermined and can be tailored to the type of monitoring performed. For example, in FIG. 7 the list 702 includes events pertinent to intracranial pressure monitoring. For example, the "Core Temperature Elevated" event can indicate the results of a temperature reading made by a temperature sensor coupled to the medical monitoring device. The "CSF Drain" event can indicate that a caregiver drained cerebrospinal fluid from the patient, which can have an effect on the intracranial pressure reading. In some embodiments, the "CSF Drain" event marker can be further broken down by amount, e.g., "CSF Drain 5-10 ccs." The "ICP Level Regulated" event can indicate that an external pressure transducer (e.g., a reference pressure transducer) has been moved or adjusted by a caregiver, or that the patient has been moved. The "Mannitol Given To Patient" event, or similar events, can indicate that a caregiver has administered a particular drug to the patient. In use, a user can select an event from the list 702, e.g., via a touchscreen or pointing device. The user can enter additional information about the event, as well as the time of the event, although in some embodiments the time of the event can automatically be recorded as the time at which the event is selected on the event marking screen 700.

The user interface described with respect to FIGS. 2-7 can be realized on virtually any device, e.g., a monitoring device, personal computer, workstation, handheld computer, tablet PC, or other computing device. In many embodiments, the device will have processing circuitry for receiving data from sensors, for comparing sensor data to stored out-of-limit thresholds, and so on. A wide variety of displays, including CRTs, LCD screens, touchscreens and so on, can receive signals from a device and display the screens and other visual aspects described herein, as those skilled in the art will understand. Moreover, a wide variety of software packages can be executed on the device and/or used to develop the aforementioned screens and other elements, including, for example, Flash Macromedia, or custom software.

Figure 8:
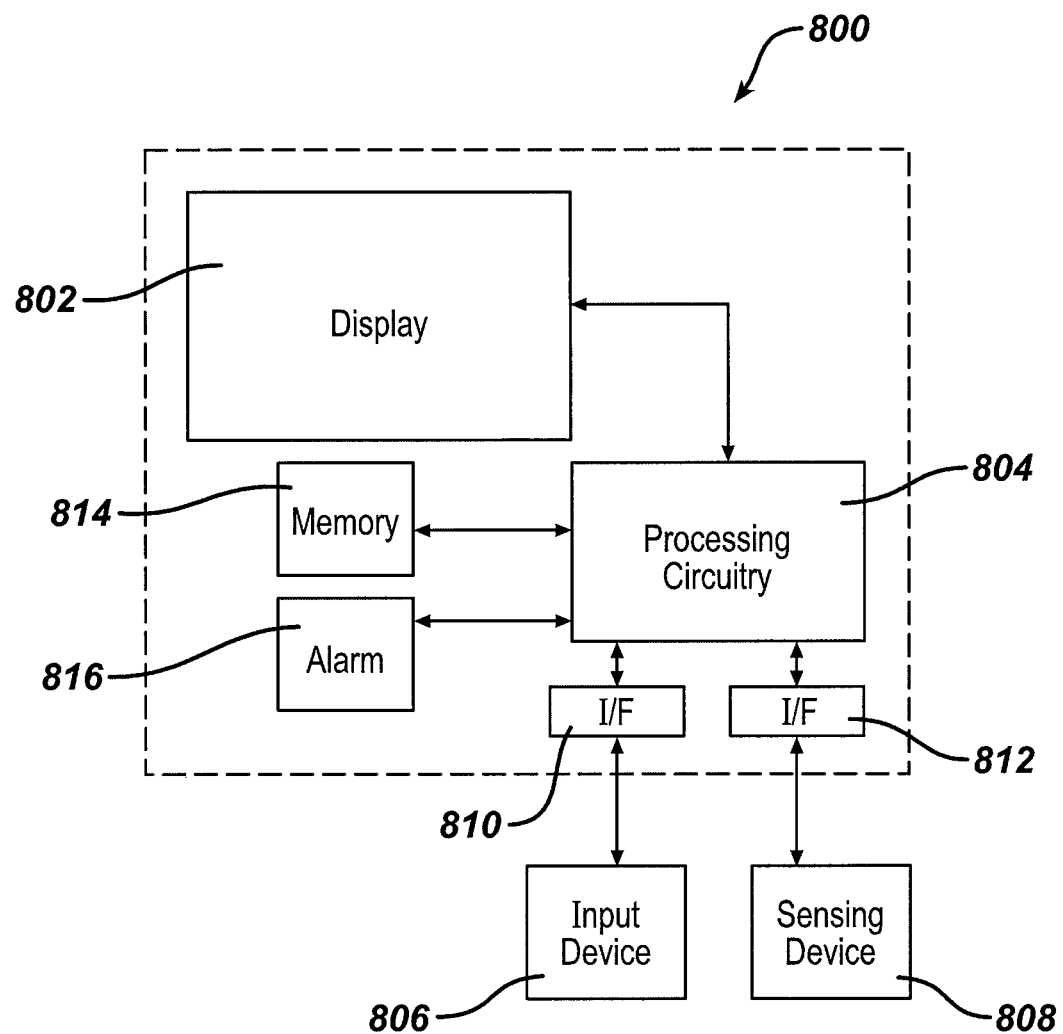
FIG. 8 schematically depicts an exemplary device for realizing the user interface shown in FIG. 1.

FIG. 8 shows one example of a device (e.g., a monitoring device) on which a user interface such as is shown in FIGS. 2-7 can be realized. The device 800 can include a display 802 for displaying screens such as those described previously. The display 802 can receive signals from processing circuitry 804, which can include a processor, video card, and/or virtually any type of electronic circuitry. The processing circuitry 804 can execute software to draw appropriate screens in response to data from one or more input devices 806, e.g., representing user input, and/or data from one or more sensing devices 808. Although shown as separate devices, the input devices 806 and sensing devices 808 can be integrated into the device 800. The input devices 806 can include pointing devices, keyboards, buttons, microphones, soft-keys, touchscreens and so on. The input devices 806 can be communicatively coupled to the processing circuitry 804 via a device interface 810. Sensing devices 808 can include ICP transducers, temperature sensors, blood pressure monitors, pulse oximeters, or virtually any other device adapted to sense and report on a physiological parameter. Sensing devices can be communicatively coupled to the processing circuitry via a device interface 812. Memory 814 can be coupled to the processing circuitry 804 for storing a wide variety of data, such as monitoring software, data from the sensing devices 808, out-of-limit or alarm thresholds, and/or patient data. In addition, the device 800 can include an alarm mechanism 816, e.g., for providing an audible or visual alarm.

One skilled in the art will appreciate further features and advantages based on the above-described embodiments. Accordingly, the application is not to be limited by what has been particularly shown and described, except as indicated by the appended claims. All publications and references cited herein are expressly incorporated herein by reference in their entirety.

What is claimed is:

1. A method for monitoring a physiological parameter, comprising:
  receiving data representing a value of a physiological parameter over time with processing circuitry operatively connected to a display, the physiological parameter being measured from a patient and comprising intracranial pressure, the processing circuitry configured to perform the steps of:
    displaying a current value screen on the display in a first window on a monitoring screen on the display;
    displaying a trend screen on the display in a second, different window on the monitoring screen that is displaying the current value screen;
    drawing, on the current value screen, a graphical representation of the value of the physiological parameter over a first time period;
    determining a mean value of the physiological parameter over time;
    drawing, on the trend screen, a graphical representation of the mean value of the physiological parameter over a second time period, the first time period having a duration shorter than the second time period;
    drawing, superimposed on the graphical representation of the mean value on the trend screen, a threshold line indicating a predetermined value;
    drawing, on the current value screen, a graphical representation of the mean value of the physiological parameter over a third time period in response to a user input that changes the first time period to the third time period; and
    drawing, on the trend screen, a graphical representation of the mean value of the physiological parameter over a fourth time period in response to a user input that changes the second time period to the fourth time period.

2. The method of claim 1, wherein the graphical representation drawn on the current value screen comprises a graph line, and further comprising shading a region between the graph line and a threshold line that corresponds to a predetermined threshold to indicate an out-of-limit condition for the physiological parameter.

3. The method of claim 1, wherein the graphical representation drawn on the trend screen comprises a trendline, and further comprising shading a region between the trendline and the threshold line to indicate an out-of-limit condition for the physiological parameter.

4. The method of claim 1, further comprising:
  comparing a value of the physiological parameter at a point in time to a threshold value to detect an out-of-limit condition, the out-of-limit condition occurring when the value of the physiological parameter exceeds the threshold value,
  wherein the display of the trend screen occurs only when the out-of-limit condition is detected.

5. The method of claim 1, further comprising:
  marking the graphical representation of the mean value of the physiological parameter with an event marker disposed at a time at which a medically-related event occurred, the time falling within the second time period.

6. A user interface for a medical monitoring device, comprising:
  a display;
  processing circuitry operatively connected to the display and configured to cause the display to show:
    a current value screen for displaying a graphical representation of a value of a physiological parameter over a first time period, the physiological parameter being measured from a patient;
    a trend screen for displaying a graphical representation of a mean value of the physiological parameter calculated over a time period including multiple heartbeats over a second time period, and for displaying a threshold line indicating a predetermined value, the threshold line being superimposed on the graphical representation of the mean value on the trend screen, the current value screen and the trend screen each being displayed together as part of a monitoring screen; and
    a historical trend screen for displaying on the monitoring screen a graphical representation of a mean value of the physiological parameter that is calculated over at least a third time period that precedes the second time period,
  wherein the physiological parameter comprises intracranial pressure.

7. The user interface of claim 6, wherein:
  the graphical representation of the value of the physiological parameter on the current value screen is a graph line, and the current value screen is adapted to indicate an out-of-limit condition for those times when the value of the physiological parameter exceeds a predetermined threshold by shading a region between the graph line and the threshold line.

8. The user interface of claim 6, wherein:
  the graphical representation of the mean value of the physiological parameter on the trend screen is a trendline, and the trend screen indicates an out-of-limit condition for those times when the mean value of the physiological parameter exceeds a predetermined threshold by shading a region between the trendline and the threshold line.

9. The user interface of claim 6, further comprising:
an input device for receiving user input to select a length of the second time period, wherein the trend screen is configured to display the graphical representation of the mean value of the physiological parameter over the user-selected second time period.

10. The user interface of claim 6, further comprising:
processing circuitry for comparing a value of the physiological parameter at a point in time to a threshold value to detect an out-of-limit condition, and for sending signals to the monitoring screen to display the trend screen only when the processing circuitry detects the out-of-limit condition.

11. The user interface of claim 6, further comprising:
an event marker disposed on the graphical representation displayed on the trend screen, the event marker disposed at a point corresponding to a time at which a medically-related event occurred, the time falling within the second time period.

12. A method for monitoring a physiological parameter, comprising:
receiving data representing a value of a physiological parameter over time with processing circuitry operatively connected to a display, the physiological parameter being measured from a patient, the processing circuitry configured to perform the steps of:
displaying together on the display, on a monitoring screen, a current value screen and a trend screen;
drawing, on the current value screen, a graphical representation of the value of the physiological parameter over a first time period;
determining a plurality of mean values of the physiological parameter, each mean value calculated over multiple patient heartbeats;
drawing, on the trend screen, a graphical representation of the plurality of mean values of the physiological parameter over a second time period, the graphical representation of the plurality of mean values only being displayed when the physiological parameter is in an out-of-limit condition in which the measured physiological parameter exceeds a predetermined threshold value.

13. The method of claim 1, further comprising:
displaying a current average value of the physiological parameter, a predetermined upper threshold limit for the physiological parameter, and a predetermined lower threshold limit for the physiological parameter on the monitoring screen together with the current value screen and the trend screen;
dynamically determining as the current average value changes as more data is received representing the value of the physiological parameter if the current average value is above the predetermined upper threshold limit or is below the predetermined lower threshold limit; and
providing an alarm on the monitoring screen if the current average value is determined to be above the predetermined upper threshold limit or is determined to be below the predetermined lower threshold limit.

* * * * *